United States Patent
Quearry

(10) Patent No.: US 10,299,812 B2
(45) Date of Patent: May 28, 2019

(54) MEDICAL DEVICE SNARE

(71) Applicant: Cook Medical Technologies LLC, Bloomington, IN (US)

(72) Inventor: Benjaman B. Quearry, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 283 days.

(21) Appl. No.: 15/132,478

(22) Filed: Apr. 19, 2016

(65) Prior Publication Data

US 2016/0354097 A1    Dec. 8, 2016

Related U.S. Application Data

(60) Provisional application No. 62/171,281, filed on Jun. 5, 2015.

(51) Int. Cl.
| | | |
|---|---|---|
| *A61B 17/00* | (2006.01) | |
| *A61B 17/22* | (2006.01) | |
| *A61B 17/221* | (2006.01) | |

(52) U.S. Cl.
CPC .. *A61B 17/221* (2013.01); *A61B 2017/00367* (2013.01); *A61B 2017/00424* (2013.01); *A61B 2017/00845* (2013.01); *A61B 2017/2217* (2013.01); *A61B 2017/22035* (2013.01)

(58) Field of Classification Search
CPC ............ A61B 17/221; A61B 17/32056; A61B 2017/00353; A61B 2017/22035; A61B 2017/2212; A61B 2017/2215; A61B 2017/2217; A61B 2018/1407; A61B 2018/141; A61B 2017/22; A61B 2017/22031; A61B 2017/30; A61B 2017/32058; A61B 2018/245; A61M 2025/0163

See application file for complete search history.

(56) References Cited

U.S. PATENT DOCUMENTS

| | | |
|---|---|---|
| RE28,969 E | 9/1976 | Naito |
| 4,286,786 A | 9/1981 | Papadopoulos |
| 5,138,750 A | 8/1992 | Gundlach et al. |
| 5,203,772 A | 4/1993 | Hammerslag et al. |
| 5,795,325 A | 8/1998 | Valley et al. |
| 6,004,279 A | 12/1999 | Crowley et al. |
| 6,878,106 B1 | 4/2005 | Herrmann |
| 7,029,178 B2 | 4/2006 | Gzybowski |

(Continued)

FOREIGN PATENT DOCUMENTS

EP    1 532 999 A2    5/2005

OTHER PUBLICATIONS

Extended European Search Report in corresponding European Application No. 16160680.1, dated Jul. 29, 2016, 9 pages.

(Continued)

*Primary Examiner* — Martin T Ton
(74) *Attorney, Agent, or Firm* — Brinks Gilson & Lione

(57) ABSTRACT

According to one example a medical device snare is described that may comprise a first strip and a second strip, each having an interlock feature. The first interlock feature configured as a groove and the second interlock feature configured as a rail may be interlocked such that the first strip and the second strip are slidable parallel to one another so a snare portion may form a loop.

22 Claims, 9 Drawing Sheets

(56) References Cited

U.S. PATENT DOCUMENTS

| | | |
|---|---|---|
| 7,951,072 B2 | 3/2011 | Adams et al. |
| 7,947,000 B2 | 5/2011 | Vargas et al. |
| 8,070,693 B2 | 12/2011 | Ayala et al. |
| 8,167,822 B2 | 5/2012 | Hardin |
| 8,845,522 B2 | 9/2014 | McIntyre et al. |
| 2007/0123804 A1* | 5/2007 | Ayala ................ A61M 25/0147 600/585 |
| 2008/0249357 A1* | 10/2008 | Soetermans ....... A61B 1/00073 600/114 |
| 2009/0163896 A1* | 6/2009 | Kumate ............... A61B 17/221 606/1 |
| 2010/0234862 A1* | 9/2010 | Patel ................ A61B 17/12009 606/151 |
| 2010/0324483 A1 | 12/2010 | Rozenberg et al. |
| 2016/0022291 A1* | 1/2016 | Johnson .................. A61B 8/12 606/113 |

OTHER PUBLICATIONS

Non-Final Office Action, dated Nov. 16, 2017, pp. 1-19, issued in U.S. Appl. No. 15/064,243, U.S. Patent and Trademark Office, Alexandria, VA.

Final Office Action, dated May 25, 2018, pp. 1-14, issued in U.S. Appl. No. 15/064,243, U.S. Patent and Trademark Office, Alexandria, VA.

\* cited by examiner

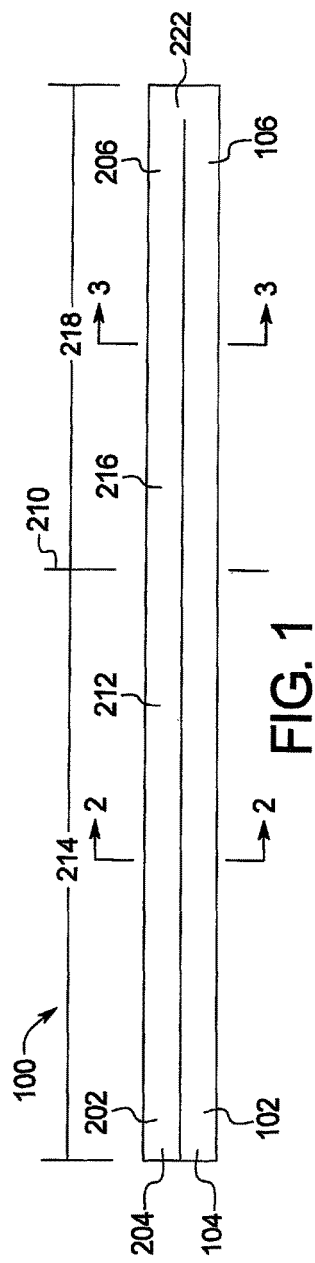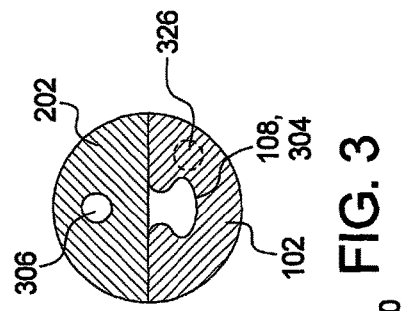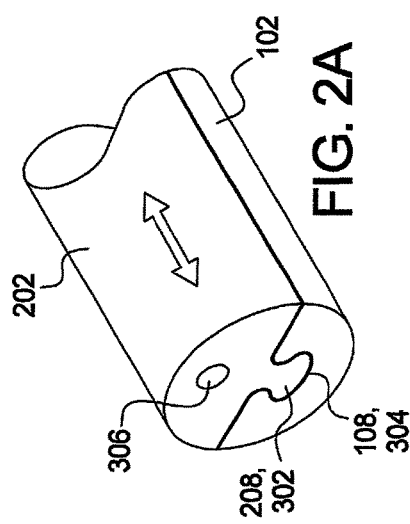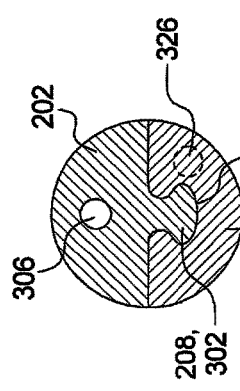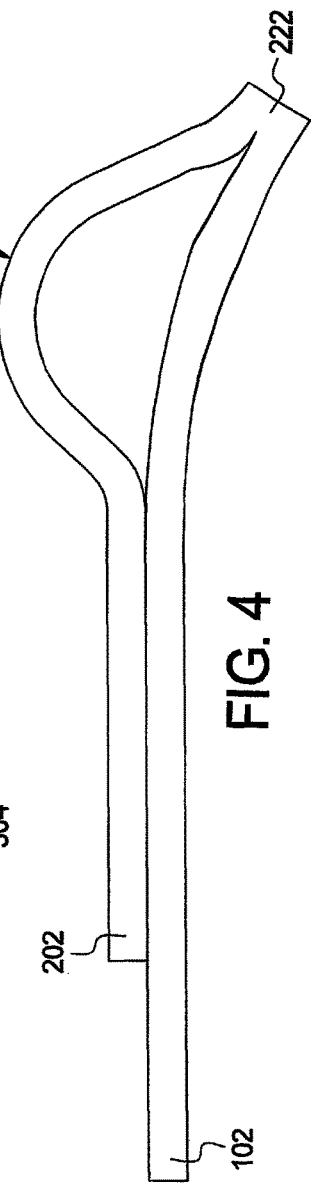

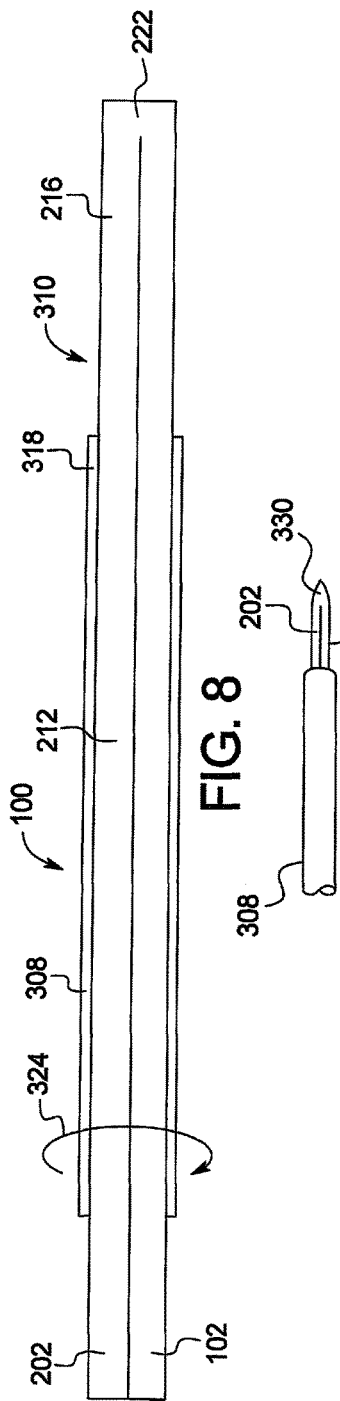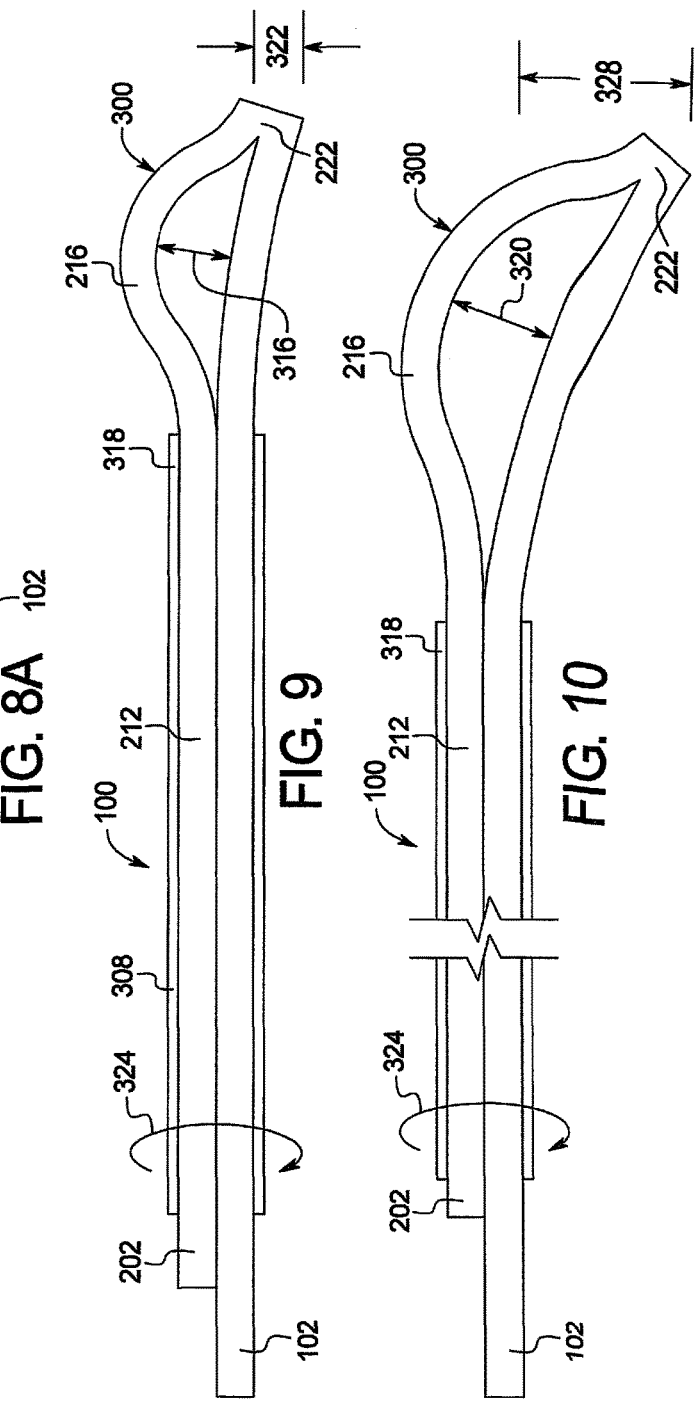

MEDICAL DEVICE SNARE

CROSS REFERENCE TO RELATED APPLICATIONS

This application claims the benefit of Provisional patent application 62/171,281 filed on Jun. 5, 2015 entitled "MEDICAL DEVICE SNARE" the entire contents of which are incorporated herein by reference.

FIELD

A medical device snare is described. It may be used to snare objects in body passageways, for example blood vessels, the biliary duct, and the urinary tract.

SUMMARY

According to one example a medical device snare is described that may comprise a first strip and a second strip, each having an interlock feature. The first interlock feature configured as a groove and the second interlock feature configured as a rail may be interlocked such that the first strip and the second strip are slidable parallel to one another so a snare portion may form a loop. Both methods and devices are described.

BRIEF DESCRIPTION OF THE DRAWINGS

FIG. 1 presents an example of a snare in an unexpanded configuration;

FIG. 2 presents a cross section taken along line 2-2 of FIG. 1;

FIG. 2A presents a perspective view of a portion of the FIG. 1 snare;

FIG. 3 presents a cross section taken along line 3-3 of FIG. 1;

FIG. 4 presents the FIG. 1 snare in an expanded configuration;

FIG. 8 presents an example of a snare with a sheath partially withdrawn;

FIG. 8A presents an example of a snare with an atraumatic tip;

FIG. 9 presents an example of the FIG. 8 snare in an expanded configuration;

FIG. 10 presents an example of the FIG. 8 snare in a greater expanded configuration;

DESCRIPTION

Figure 5:
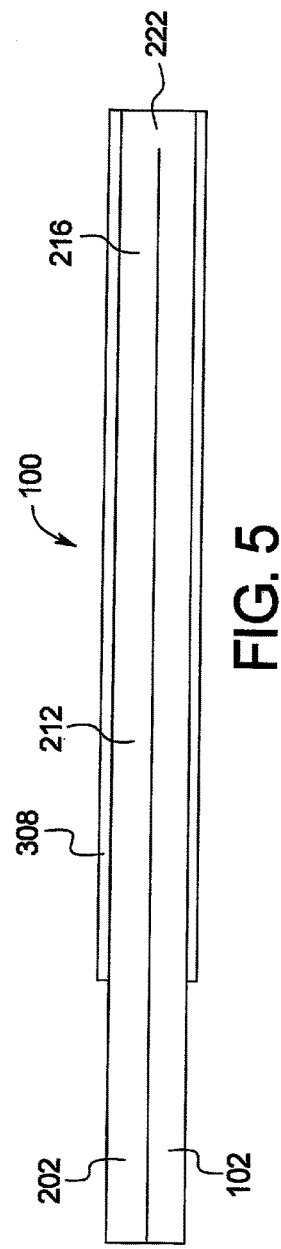
FIG. 5 presents an example of a snare with a sheath.

Various aspects of examples are presented in FIGS. 1-19, which are not drawn to any particular scale, and wherein like components in the numerous views are numbered alike. An example of a medical device snare 100 is presented in FIG. 1. The medical device snare comprises a first strip 102 extending from a first proximal end 104 to a first distal end 106 and has a first interlock feature configured as a groove 108 extending from proximate the first proximal end 104 to the first distal end 106. The first interlock feature configured as a groove 108 is shown in FIGS. 2 and 3. Referring again to FIG. 1, a second strip 202 extends from a second proximal end 204 to a second distal end 206 and has an intermediate location 210. The second strip 202 has a strip portion 212 with a second interlock feature configured as a rail 208 extending from the second proximal end 204 and ending at the intermediate location 210. The second interlock feature configured as a rail 208 is shown in FIG. 2 and is absent in FIG. 3, having ended at the intermediate location 210.

As used herein, strip means a long narrow piece of a material suitable for use in a snare. Polymers such as vinyl, urethane, polyethylene and others or a metal such as tungsten, titanium, barium and others may be implemented. Polymers are desirable for use with magnetic resonance imaging. Other materials may be useful for fluoroscopic or ultrasound imaging. Interlock, interlocking, or interlocked means two strips engaged with each other by fitting together the rail within the groove. They are unable to separate laterally, but can move relative to each other in parallel. The groove restrains the rail from lateral separation. Lateral means transverse to the longitudinal length of the first strip 102 and the second strip 202.

The second interlock feature configured as a rail 208 may be formed separately and bonded or otherwise fixed to the second strip 202. In one example they are integrally formed with their respective strips by molding for example. They may be formed by extrusion. Molding and extrusion have the benefit of providing a very strong connection. Referring again to FIG. 1, the strip portion 212 defines a strip portion longitudinal length 214, the second strip 202 has a snare portion 216 extending from the intermediate location 210 to the second distal end 206. The snare portion 216 defines a snare portion longitudinal length 218. The second interlock feature configured as a rail 208 ends at the intermediate location 210 so that the snare portion 216 is free to move laterally relative to the strip portion 212 and form a loop 300 as shown in FIG. 4. As mentioned previously, the second interlock feature configured as a rail 208 may be a polymer, and may be formed as an integral part of the second strip 202. In such case, the second interlock feature configured as a rail 208 may be removed from the snare portion 216 by cutting it away with a cutting tool, for example a knife or a razor blade. A jig may be used.

The strip portion longitudinal length 124 may be longer than the snare portion longitudinal length 218. The strip portion longitudinal length 214 may be at least 10 times the snare portion longitudinal length 218. It could also be 20, 30, 40, 50, or more times longer than the snare portion longitudinal length 218. The first distal end 106 and the second distal end 206 are fastened together at a joint 222 to prevent parallel movement of the first strip 102 and the second strip 202 at the joint 222. The joint may be formed as a mechanical fastener such as a pin for example, a rivet, bonding by a glue, and/or fused together if the first strip 102 and second strip 202 are formed of a thermoplastic polymer or other fusible material.

The first interlock feature configured as a groove 108 and the second interlock feature configured as a rail 208 are interlocked such that the first strip 102 and the second strip 202 are slidable parallel to one another along the strip portion 212 as shown in FIG. 2A, and by comparing FIG. 1 with FIG. 2. The snare portion 216 is not interlocked with the first strip 102 so the snare portion 216 forms a loop 300 and moves laterally when at least one of the first strip 102 and the second strip 202 slides relatively parallel to the other, as shown in FIG. 4. Which direction the first strip 102 and the second strip 202 move laterally depends which strip is placed in compression. The strip, 102 or 202, that is placed in compression relative to the other strip moves laterally in response to compressive force. In FIG. 4, the second strip 202 is slid forward toward the joint 222 and placed in compression and the joint 222 moves down. Alternatively, the first strip 102 may be slid forward toward the joint 222 and placed in compression and the joint 22 moves up.

Although other geometries are possible, one of the first interlock feature configured as a groove 108 and second interlock feature configured as a rail 208 may be a rail 302, as shown in FIG. 2, and the other may be a groove 304 configured to interlock with the rail 302, also shown in FIG. 2. The rail 302 and groove 304 may be dimensioned so that they snap together, thus remaining interlocked without applying an external force. In the example presented the second interlock feature configured as a rail 208 extends generally perpendicular to the first strip 202. In other embodiments it may extend at other angles, even horizontal, and the first interlock feature configured as a groove 108 would be oriented to receive the second interlock feature configured as a rail 208 and interlock with it.

Figure 20:
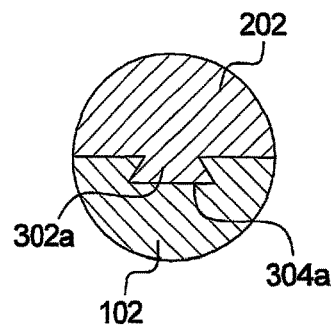
FIG. 20 presents a second interlock feature configured as a longitudinal rail with a trapezoidal cross section.
Figure 21:
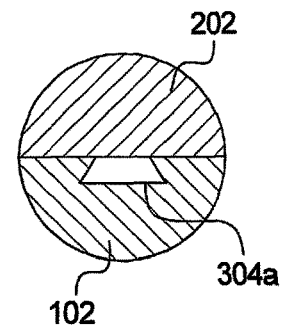
FIG. 21 shows the configuration where the longitudinal rail is removed along the snare portion.
Figure 22:
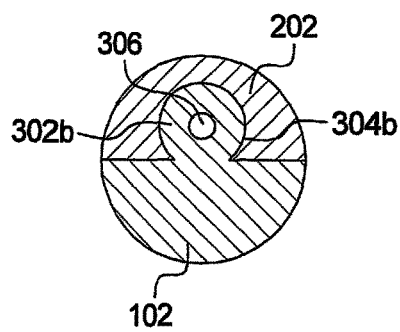
FIG. 22 presents the second interlock feature configured as a longitudinal rail with a circular cross section.
Figure 23:
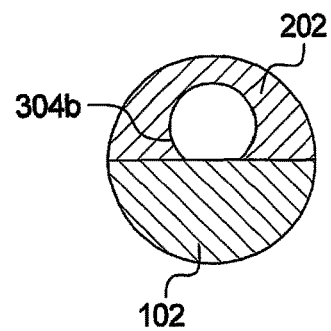
FIG. 23 presents a configuration where the cylinder is removed along the snare portion.
Figure 24:
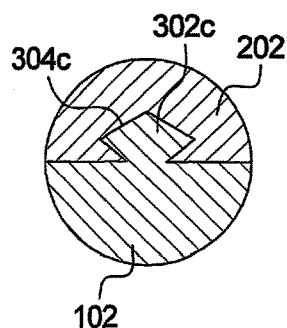
FIG. 24 presents the second interlock feature configured as a longitudinal rail with a square cross section.
Figure 25:
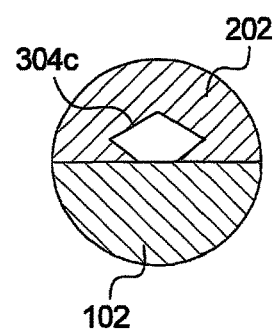
FIG. 25 presents a configuration where the longitudinal rail is removed along the snare portion.
Figure 26:
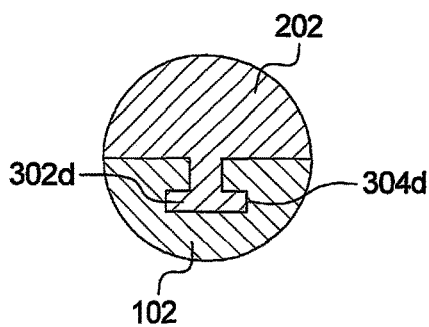
FIG. 26 presents the second interlock feature configured as a longitudinal rail with a T-shaped cross section.
Figure 27:
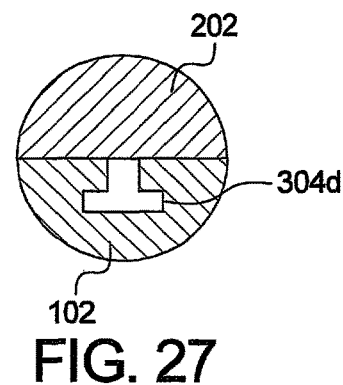
FIG. 27 shows the configuration where the longitudinal rail is removed along the snare portion.

Other examples are presented in FIGS. 20 through 27. In FIG. 20 the second interlock feature configured as a rail 208 may be a longitudinal rail 302a with a trapezoidal cross section, and the first interlock feature configured as a groove 108 may be a mating trapezoidal groove 304a. FIG. 21 shows the configuration where the longitudinal rail 302a is removed along the snare portion 216. FIG. 22 shows the second interlock feature configured as a rail 208 as a cylinder 302b, and the first interlock feature configured as a groove 108 may be a mating cylindrical groove 304b. The cylinder 302b may have a working channel 306. FIG. 23 shows the configuration where the cylinder 302b is removed along the snare portion 216. In FIG. 24 the second interlock feature configured as a rail 208 may be a longitudinal rail 302c with a square cross section, and the first interlock feature configured as a groove 108 may be a mating square groove 304c. FIG. 25 shows the configuration where the longitudinal rail 302c is removed along the snare portion 216. In FIG. 26 the second interlock feature configured as a rail 208 may be a longitudinal rail 302d with a T-shaped cross section, and the first interlock feature configured as a groove 108 may be a mating T-shaped groove 304d. FIG. 27 shows the configuration where the longitudinal rail 302d is removed along the snare portion 216.

The first strip 102 may comprise a working channel 326 extending from the first proximal end 104 to the first distal end 106. Likewise the second strip 202 may comprise a working channel 306 extending from the second proximal end 204 to the second distal end 206. The working channels 306 and 326 are lumens through which a wire guide or other medical device may be passed, for example a guide wire, biopsy forceps, an occlusion device, and/or or an angioplasty balloon, intravenous ultrasound catheter, without limitation. Contrast, cell therapy, or a drug may also be introduced at the tip of the medical device snare 100 through the working channel. The snare 100 may have a single working channel 306 or 326, both working channels 306 and 326, or additional working channels disposed in either or both of the the first strip 102 and second strip 202. The diameters of the working channels 306 and 326, respectively, may be up to ¼ the outer diameter of the snare 100.

Figure 6:
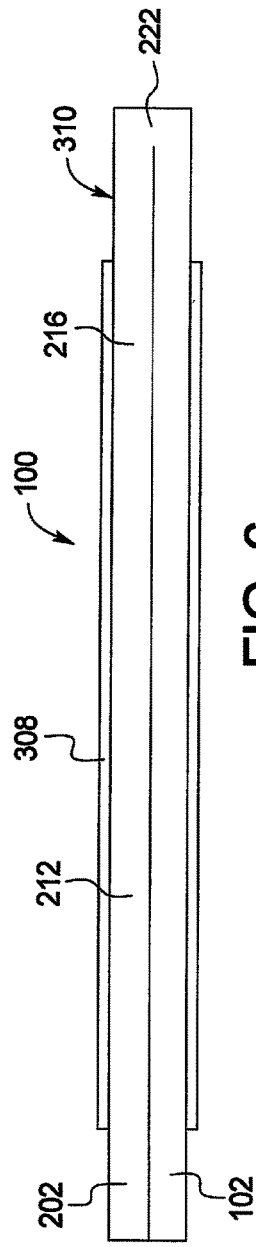
FIG. 6 presents the FIG. 5 snare with the sheath partially withdrawn.
Figure 7:
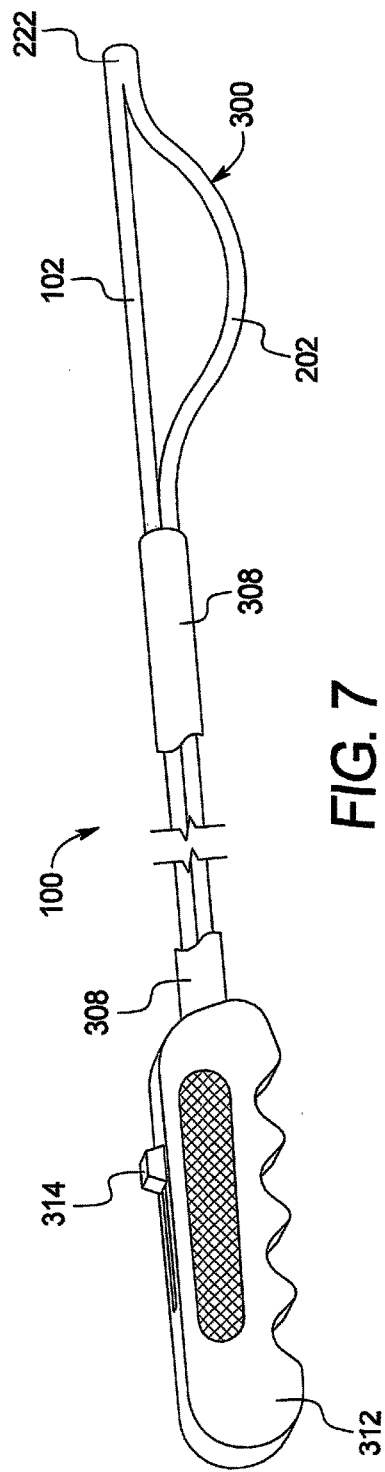
FIG. 7 presents an example of a snare with a handle.

As shown in FIGS. 5-7, the snare 100 may have a sheath 308 that covers and contains the snare 100. The first strip 102 and second strip 202 are disposed within the sheath 308. The sheath 308 may terminate proximate the joint 222 and the sheath 308 may be retractable to expose at least a part of the snare portion 216 at the joint 222. This allows the snare to expand by moving either strip 102 or 202 parallel relative to each other. The outside diameter of the snare 100 or sheath 308 may range from 4 French to 18 French in diameter. The length of the snare 100 may range up to 2 meters in length depending on the application.

Referring now to FIG. 7, a handle 312 may be fixed to one of the first strip 102 and the second strip 202. The other of the first strip 102 and the second strip 202 is fixed to an actuator 314 slidably received within the handle 312. Moving the actuator forward and backward causes the snare to expand and contract. In this example the sheath 308 is fixed to the handle. In other embodiments the sheath 308 may be configured to move longitudinally to cover and uncover the snare portion 216. A separate actuator could be implemented to do so. The strip not attached to the handle may be moved forward using the actuator 314 thereby causing the snare to expand. The length available to expand is determined by how far the snare portion 216 extends out of the tip of the sheath 308. However, the intermediate location 210 could be disposed outside of the sheath 308 and the snare would open laterally from the intermediate location 210 and forward to the joint 222. This may happen because the first strip 102 and second strip 202 are interlocked up to the intermediate location 210. They are interlocked by the first interlock feature configured as a groove 108 and the second interlock feature configured as a rail 208. They are not interlocked along the snare portion 216.

The first strip 102 and the second strip 202 may be polymeric. This is particularly advantageous for magnetic resonance imaging applications. For use with fluoroscopic imaging, the first strip 102 and the second strip 202 may be polymeric and at least a portion may be radiopaque. For ultrasound applications, the snare 100 may have at least a portion of the first strip 102 and second strip 202 that is echogenic.

FIG. 8 presents a snare 100 with the sheath partly withdrawn thereby exposing part 310 of the snare portion 216. As shown in FIG. 9, the second strip 202 may be pushed forward relative to the second strip 202. This causes the snare portion 216 outside of the sheath 318 to deflect away from the first strip 102 and create an open space having a first span 316. It also causes the tip (or joint 222) to deflect a first distance 322 in an opposite direction. As shown in FIG. 10, pushing the second strip 202 further forward causes the snare portion outside of the sheath 318 to deflect further and create an open space having a second span 320 that is greater than the first span 316. It also causes the tip (or joint 222) to deflect a second distance 328 that is greater than the first distance 322. During a procedure, for example to snare an object, the snare 100 may be twisted at any step as indicated by arrow 324.

Figure 11:
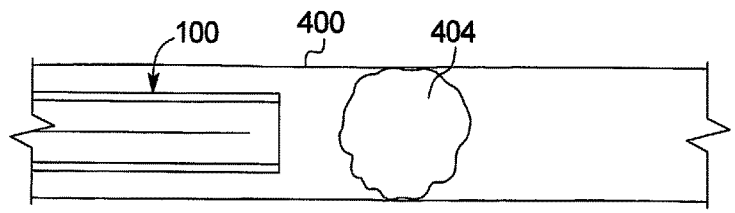
FIG. 11 presents an example of a snare having a sheath, both proximate an object in a body passageway.
Figure 12:
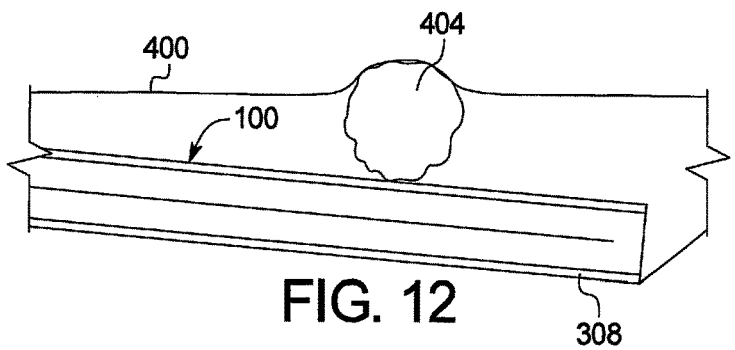
FIG. 12 presents the FIG. 11 snare and sheath disposed past the object.
Figure 13:
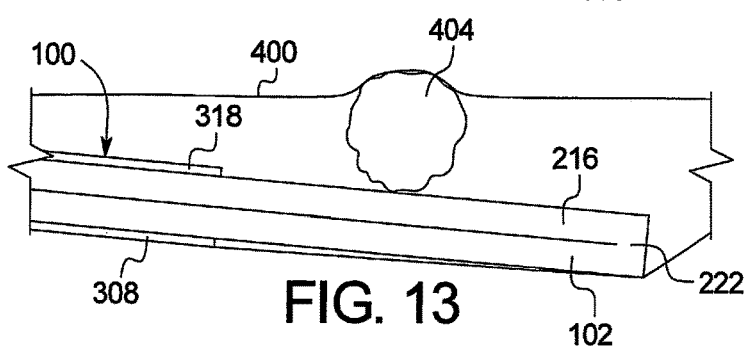
FIG. 13 presents the FIG. 11 snare with the sheath partially withdrawn.
Figure 14:
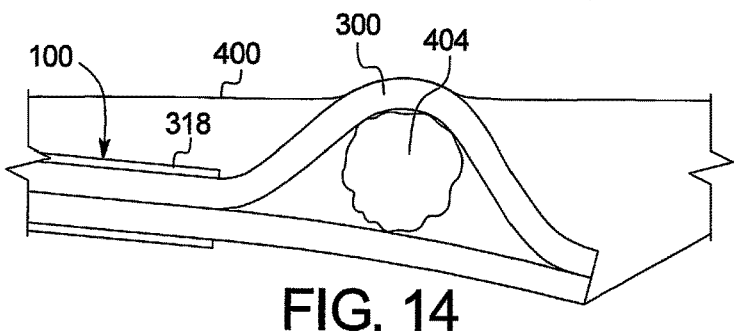
FIG. 14 presents the FIG. 11 snare with the object captured.
Figure 15:
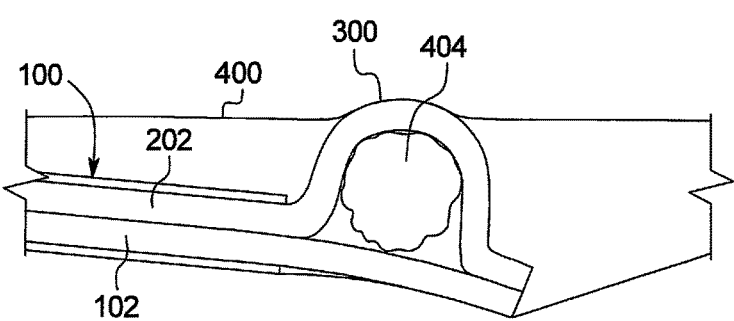
FIG. 15 presents the FIG. 11 snare with the sheath advanced to tighten a grip on the object.
Figure 16:
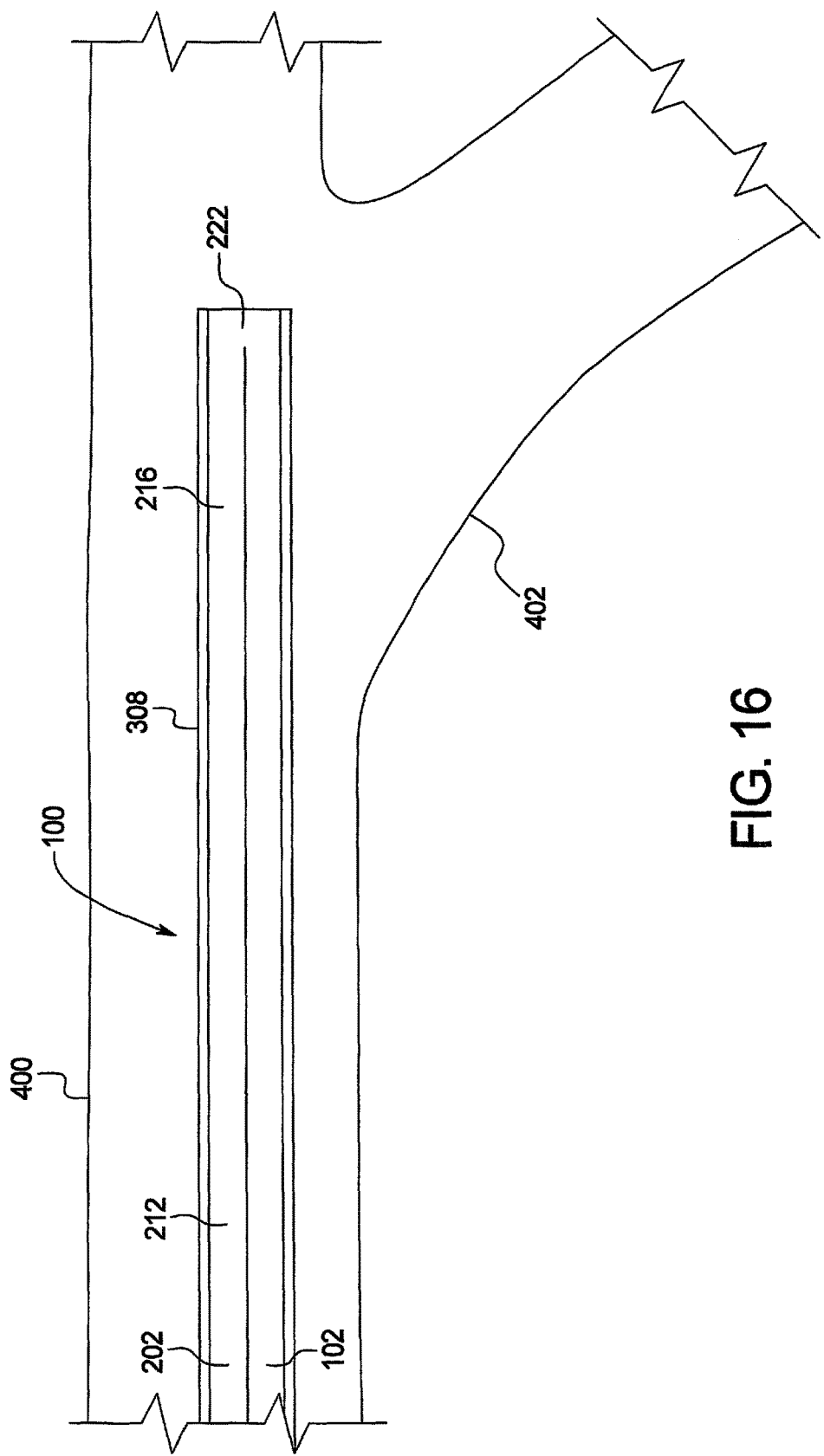
FIG. 16 presents an example of snare in a body passageway proximate a side branch.

Examples of methods are also provided. For example, with reference to FIGS. 11-15, a method for using a medical device snare 100 is presented. The snare 100 may be configured according to any of the previous examples. Referring now to FIG. 11, a first step is to insert the snare 100 into a body passageway 400, the body passageway 400 having an object 404 to be snared and placing the tip proximate the object 404. In this example the snare 100 is received within a sheath but this is optional. Next, as shown in FIG. 12, the snare 100 and sheath 308 are advanced past the object 404. Then the sheath 308 is retracted, exposing part of the first strip 102 and at least part of the snare portion 216 and the joint 222 outside of the sheath 308 at the distal sheath end 318, as shown in FIG. 13. Referring now to FIG. 14, one of the first strip 102 and the second strip 202, in this example second strip 202, is slid parallel relative to the other to form a loop 300 at the distal sheath end 318. In this example the second strip 202 is pushed forward toward the object 404 although the opposite can be done, pushing the first strip 102 forward toward the object 404. Referring again to FIG. 9, the loop 300 defines a first span 316 thereby deflecting the joint 222 a first distance 322 to a side of the sheath 308. Referring back to FIG. 14, the object 404 is trapped within the loop 300. At least one of the first strip 102 and the second strip 202 is slid parallel relative to the other to contract the loop 300 and snare the object 404 and tighten the snare around the object, as shown in FIG. 15. At this point the snare 100 may be removed from the body along with the object 404. The intermediate location 210 could be disposed outside of the sheath 308 and the snare would open laterally from the intermediate location 210 and forward to the joint 222. This may happen because the first strip 102 and second strip 202 are interlocked up to the intermediate location 210. They are interlocked by the first interlock feature configured as a groove 108 and the second interlock feature configured as a rail 208. They are not interlocked along the snare portion 216.

Figure 17:
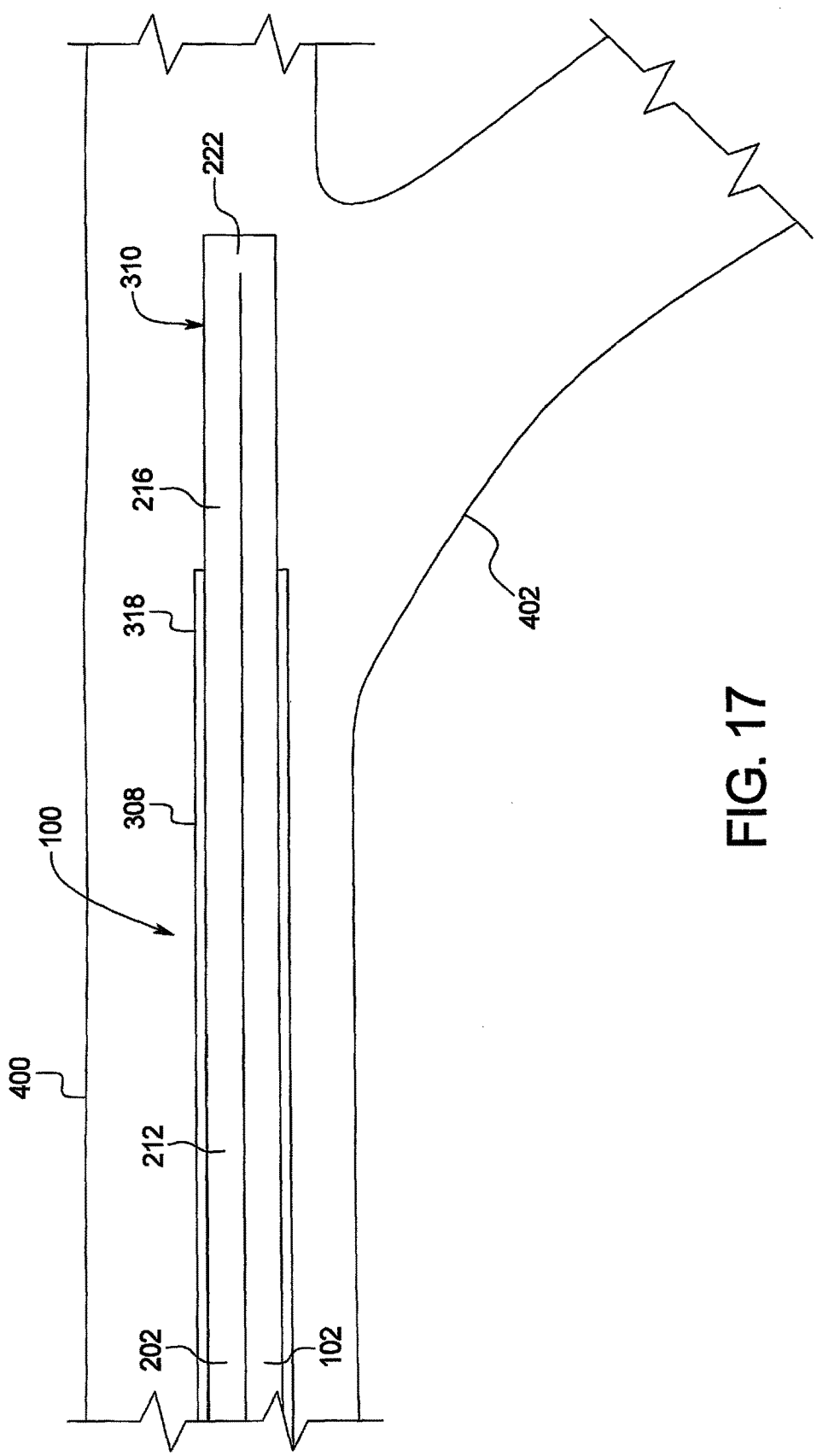
FIG. 17 presents the FIG. 16 snare with the sheath partially withdrawn.
Figure 18:
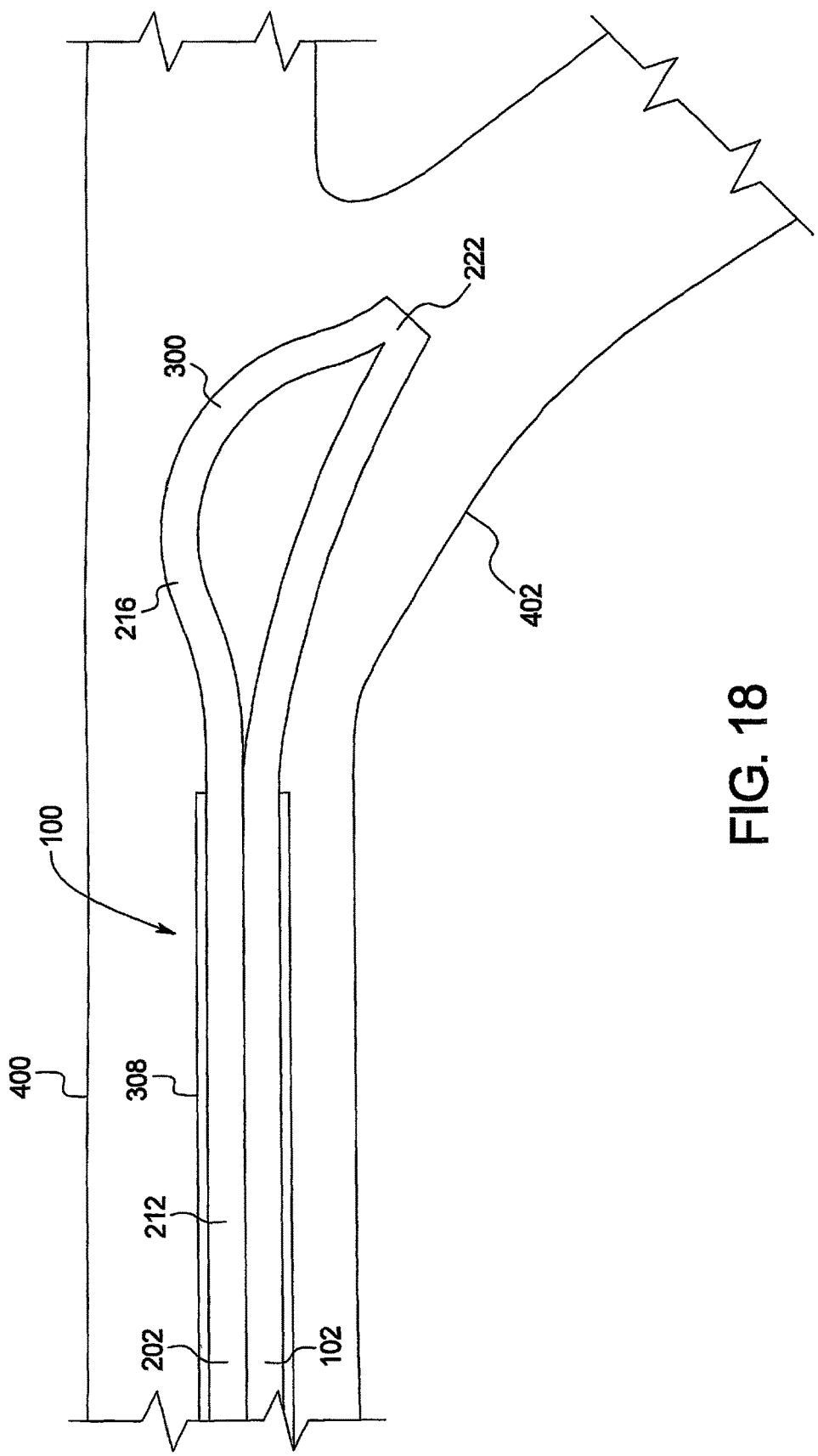
FIG. 18 presents the FIG. 16 snare with the snare partially expanded.
Figure 19:
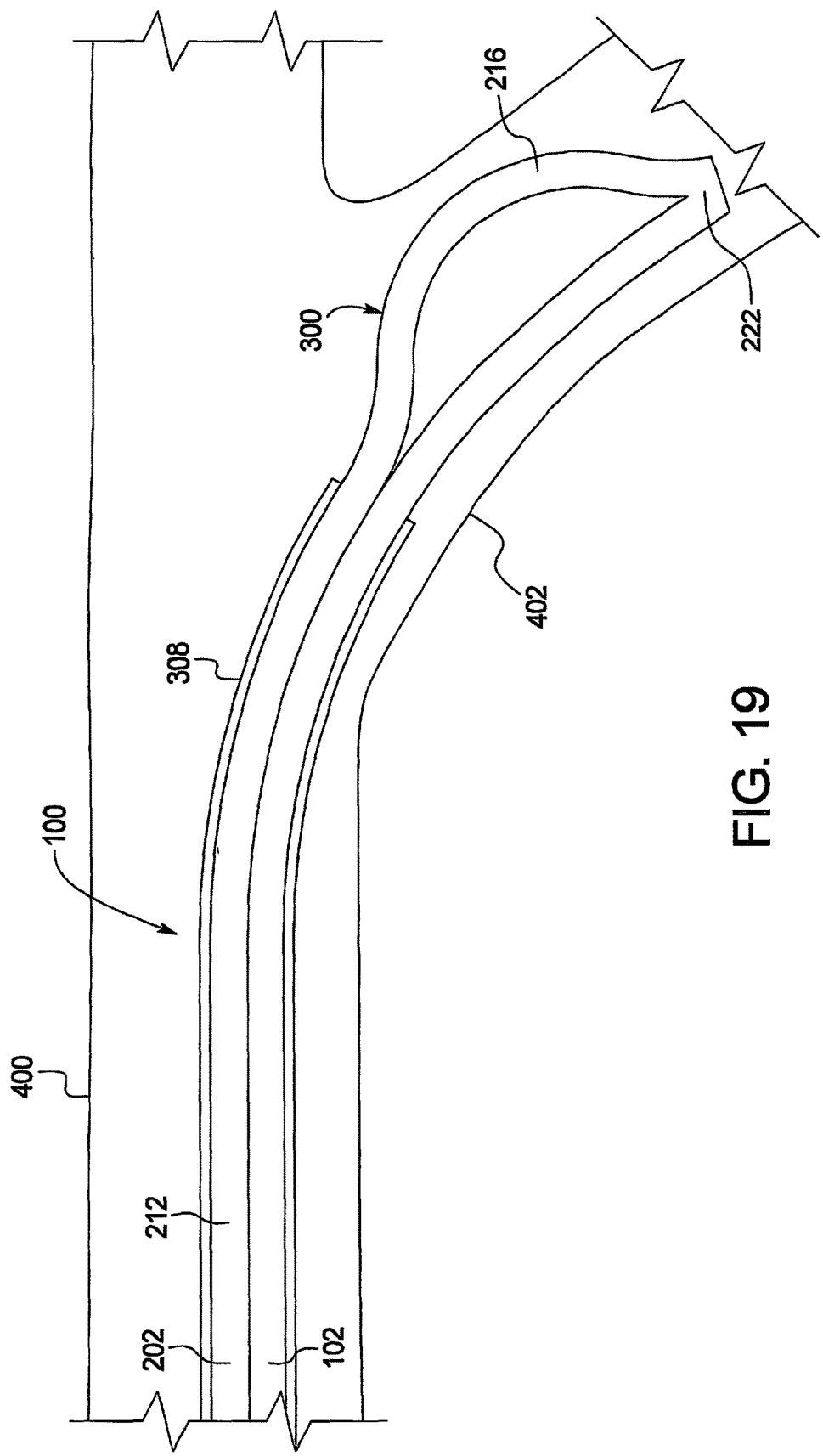
FIG. 19 presents the FIG. 16 snare advanced into the side branch.

Another example of a method for using a snare 100 is now described with reference to FIGS. 16-19. The snare 100 may be configured according to any of the previous examples. The method begins by inserting a medical device snare 100 into a body passageway 400. The body passageway 400 has a side branch 402, and the tip of the snare 100 is placed proximate the side branch 402. Next, as shown in FIG. 17, part of the first strip 102 and at least part of the snare portion 216 and the joint 222 are exposed outside of the sheath 308 at the the distal sheath end 318. At least one of the first strip 102 and the second strip 202 are slid parallel relative to the other to form the loop 300 at the distal sheath end 318, as shown in FIG. 18. Referring again to FIG. 9, the loop 300 forms a first span 316 thereby deflecting the joint 222 a first distance 322 to a side of the sheath 308 to direct the joint 222 into the side branch. Referring now to FIG. 19, the loop 300 may be pushed into the side branch 402. The sheath 308 may be pushed into the side branch 402 along with the snare 100. The snare 100 may be twisted at any point during the method.

The method may further comprise exposing a larger part of the first strip 102 and a larger part of the snare portion 216 outside of the sheath 308, sliding at least one of the first strip 102 and the second strip 202 parallel relative to the other to form the loop 300 at the distal sheath end 318 to define a second span 320 greater than the first span 316, which deflects the joint 222 a second distance 328 to the side of the sheath 308 greater than the first distance 322. This is shown in FIG. 10. The intermediate location 210 could be disposed outside of the sheath 308 and the snare would open laterally from the intermediate location 210 and forward to the joint 222. This may happen because the first strip 102 and second strip 202 are interlocked up to the intermediate location 210. They are interlocked by the first interlock feature configured as a groove 108 and the second interlock feature configured as a rail 208. They are not interlocked along the snare portion 216 because the rail 208 is absent.

Various rail and groove configurations are possible. A few examples are presented in FIGS. 20 through 27. In FIG. 20, a configuration is presented where the rail 302 has a trapezoidal configuration 302*a* and the groove has a mating trapezoidal configuration 304*a*. FIG. 21 presents the FIG. 20 configuration with the rail 208 absent, as along the snare portion 216. FIGS. 22 and 23 show a similar configuration with a rail 302*b* having a circular cross section and the groove 304*b* having a circular mating configuration. FIG. 23 presents the FIG. 22 configuration with the rail 208 absent, as along the snare portion 216. FIGS. 24 and 25 show a similar configuration with a rail 302*c* having a diamond cross section and the groove 304*c* having a mating diamond configuration. FIG. 25 presents the FIG. 24 configuration with the rail 208 absent, as along the snare portion 216. FIGS. 26 and 27 show a similar configuration with a rail 302*d* having a T cross section and the groove 304*c* having a mating T configuration. FIG. 27 presents the FIG. 26 configuration with the rail 208 absent, as along the snare portion 216.

Although shown implemented with the sheath 308, it is optional and the various examples presented herein may be implemented without it.

Various currently contemplated examples follow:

Example 1

With reference to FIGS. 1-3, an example of a medical device snare 100 such as medical device snare 100 is presented, comprising:

a first strip such as first strip 102 extending from a first proximal end such as first proximal end 104 to a first distal end such as first distal end 106 and having a first interlock feature configured as a groove such as first interlock feature configured as a groove 108 extending from proximate the first proximal end 104 to the first distal end 106;

a second strip 202 extending from a second proximal end 204 to a second distal end 206 and having an intermediate location 210, the second strip 202 having a strip portion 212 with a second interlock feature configured as a rail 208 extending from the second proximal end 204 and ending at the intermediate location 210, the strip portion 212 defining a strip portion 212 longitudinal length, the second strip 202 having a snare portion 216 extending from the intermediate location 210 to the second distal end 206, the snare portion 216 defining a snare portion 216 longitudinal length, the strip portion 212 longitudinal length being at least ten times the snare portion 216 longitudinal length, the first distal end 106 and the second distal end 206 being fastened together at a joint 222 to prevent parallel movement of the first strip 102 and the second strip 202 at the joint 222; and, wherein the first interlock feature configured as a groove 108 and the second interlock feature configured as a rail 208 are interlocked such that the first strip 102 and the second strip 202 are slidable parallel to one another along the strip portion 212, and the snare portion 216 is not interlocked with the first strip 102 so the snare portion 216 forms a loop 300 when at least one of the first strip 102 and the second strip 202 slides relatively parallel to the other.

Example 2

The medical device snare 100 of Example 1, wherein one of the first interlock feature configured as a groove 108 and second interlock feature configured as a rail 208 is a rail 302 and the other is a groove 304 configured to interlock with the rail 302, as shown in FIGS. 2 through 3. This may be implemented with the elements of Examples 3 through 10 alternatively or in addition to one another.

Example 3

The medical device snare 100 of Example 1, wherein the first strip 102 comprises a working channel 326 extending from the first proximal end 104 to the first distal end 106, as shown in FIGS. 2 and 3. This may be implemented with the elements of Example 2 and Examples 4 through 10 alternatively or in addition to one another.

Example 4

The medical device snare 100 of Example 1, wherein the second strip 202 comprises a working channel 306 extending from the second proximal end 204 to the second distal end 206. This may be implemented with the elements of Examples 2 and 3 and Examples 5 through 10 alternatively or in addition to one another.

Example 5

The medical device snare 100 of Example 1, comprising a sheath 308, the first strip 102 and second strip 202 being disposed within the sheath 308. This may be implemented with the elements of Examples 2 through 4 and Examples 6 through 10 alternatively or in addition to one another.

Example 6

The medical device snare 100 of Example 1, comprising a sheath 308, the sheath 308 terminating proximate the joint 222, the sheath 308 being retractable to expose at least a part 310 of the snare portion 216. This may be implemented with the elements of Examples 2 through 5 and Examples 7 through 10 alternatively or in addition to one another.

Example 7

The medical device snare 100 of Example 1, wherein the first strip 102 and the second strip 202 are polymeric. This may be implemented with the elements of Examples 2 through 6 and Examples 8 through 10 alternatively or in addition to one another.

Example 8

The medical device snare 100 of Example 1, wherein the first strip 102 and the second strip 202 are polymeric and at least a portion is radiopaque. This may be implemented with the elements of Examples 2 through 7 and Examples 9 and 10 alternatively or in addition to one another.

Example 9

The medical device snare 100 of Example 1, wherein at least a portion of the first strip 102 and second strip 202 are echogenic. This may be implemented with the elements of Examples 2 through 8 and Example 10 alternatively or in addition to one another.

Example 10

The medical device snare 100 of Example 1, comprising a handle 312 fixed to one of the first strip 102 and the second strip 202, and the other of the first strip 102 and the second strip 202 is fixed to an actuator 314 slidably received within the handle 312. This may be implemented with the elements of Examples 2 through 9 alternatively or in addition to one another.

Example 11

A method for using a medical device snare 100:
inserting a medical device snare 100 into a body passageway 400, the body passageway 400 having an object 404:
  a first strip 102 extending from a first proximal end 104 to a first distal end 106 and having a first interlock feature configured as a groove 108 extending from proximate the first proximal end 104 to the first distal end 106;
  a second strip 202 extending from a second proximal end 204 to a second distal end 206 and having an intermediate location 210, the second strip 202 having a strip portion 212 with a second interlock feature configured as a rail 208 extending from the second proximal end 204 and ending at the intermediate location 210, the strip portion 212 defining a strip portion 212 longitudinal length, the second strip 202 having a snare portion 216 extending from the intermediate location 210 to the second distal end 206, the snare portion 216 defining a snare portion 216 longitudinal length, the strip portion 212 longitudinal length being at least ten times the snare portion 216 longitudinal length, the first distal end 106 and the second distal end 206 being fastened together at a joint 222 to prevent parallel movement of the first strip 102 and the second strip 202 at the joint 222; and,
wherein the first interlock feature configured as a groove 108 and the second interlock feature configured as a rail 208 are interlocked such that the first strip 102 and the second strip 202 are slidable parallel to one another along the strip portion 212, and the snare portion 216 is not interlocked with the first strip 102 so the snare portion 216 forms a loop 300 when at least one of the first strip 102 and the second strip 202 slides relatively parallel to the other; and a sheath 308 extending from a proximal sheath 308 end to a distal sheath end 318, the first strip 102 with the snare portion 216 being disposed within the sheath 308 with the joint 222 proximal the distal sheath end 318;

exposing part 310 of the first strip 102 and at least part 310 of the snare portion 216 and the joint 222 outside of the sheath 308 at the distal sheath end 318;

sliding at least one of the first strip 102 and the second strip 202 parallel relative to the other to form the loop 300 at the distal sheath end 318, the loop 300 defining a first span 316 thereby deflecting the joint 222 a first distance 322 to a side of the sheath 308;

snare the object 404; and, sliding the at least one of the first strip 102 and the second strip 202 parallel relative to the other to contract the loop 300 around the object.

Example 12

The method of Example 11, wherein one of the first interlock feature configured as a groove 108 and second interlock feature configured as a rail 208 is a rail 302 and the other is a groove 304 configured to interlock with the rail 302. This may be implemented with the elements of Example 13 alternatively or in addition to one another.

Example 13

The method of Example 11 comprising a handle 312 fixed to one of the first strip 102 and the second strip 202, and the other of one of the first strip 102 and second strip 202 is fixed to an actuator 314 slidably received within the handle 312. This may be implemented with the elements of Example 12 alternatively or in addition to one another.

Example 14

A method for using a medical device snare 100, comprising:
inserting a medical device snare 100 into a body passageway 400, the body passageway 400 having a side branch 402, the medical device snare 100 comprising:
a first strip 102 extending from a first proximal end 104 to a first distal end 106 and having a first interlock feature configured as a groove 108 extending from proximate the first proximal end 104 to the first distal end 106;
a second strip 202 extending from a second proximal end 204 to a second distal end 206 and having an intermediate location 210, the second strip 202 having a strip portion 212 with a second interlock feature configured as a rail 208 extending from the second proximal end 204 and ending at the intermediate location 210, the strip portion 212 defining a strip portion 212 longitudinal length, the second strip 202 having a snare portion 216 extending from the intermediate location 210 to the second distal end 206, the snare portion 216 defining a snare portion 216 longitudinal length, the strip portion 212 longitudinal length being at least ten times the snare portion 216 longitudinal length, the first distal end 106 and the second distal end 206 being fastened together at a joint 222 to prevent parallel movement of the first strip 102 and the second strip 202 at the joint 222; and,
wherein the first interlock feature configured as a groove 108 and the second interlock feature configured as a rail 208 are interlocked such that the first strip 102 and the second strip 202 are slidable parallel to one another along the strip portion 212, and the snare portion 216 is not interlocked with the first strip 102 so the snare portion 216 forms a loop 300 when at least one of the first strip 102 and the second strip 202 slides relatively parallel to the other; and a sheath 308 extending from a proximal sheath 308 end to a distal sheath end 318, the first strip 102 and the snare portion 216 being disposed within the sheath 308 with the joint 222 proximal the distal sheath end 318;

exposing part 310 of the first strip 102 and at least part 310 of the snare portion 216 and the joint 222 outside of the sheath 308 at the distal sheath end 318;

sliding at least one of the first strip 102 and the second strip 202 parallel relative to the other to form the loop 300 at the distal sheath end 318, the loop 300 defining a first span 316 thereby deflecting the joint 222 a first distance 322 to a side of the sheath 308 to direct the joint 222 into the side branch 402.

Example 15

The method of Example 14, comprising pushing the loop 300 into the side branch 402. This may be implemented with the elements of Examples 16 through 20 alternatively or in addition to one another.

Example 16

The method of Example 14, comprising pushing the loop 300 and the sheath 308 into the side branch 402. This may be implemented with the elements of Example 15 and Examples 17 through 20 alternatively or in addition to one another.

Example 17

The method of Example 14, comprising twisting 324 the medical device snare 100. This may be implemented with the elements of Examples 15 and 16 and Examples 18 through 20 alternatively or in addition to one another.

Example 18

The method of Example 14, wherein one of the first interlock feature configured as a groove 108 and second interlock feature configured as a rail 208 is a rail 302 and the other is a groove 304 configured to interlock with the rail 302. This may be implemented with the elements of Examples 15 through 17 and Examples 19 and 20 alternatively or in addition to one another.

Example 19

The method of Example 14, comprising a handle 312 fixed to one of the first strip 102 and the second strip 202, and the other one of the other first strip 102 and the second strip 202 is fixed to an actuator 314 slidably received within the handle 312. This may be implemented with the elements of Examples 15 through 18 and Example 20 alternatively or in addition to one another.

Example 20

The method of Example 14, comprising:
exposing a larger part 310 of the first strip 102 102 and a larger part 310 of the snare portion 216 216 outside of the sheath 308 308;
sliding at least one of the first strip 102 and the second strip 202 parallel relative to the other to form the loop 300 at the distal sheath end 318 to define a second span 320 greater than the first span 316, and thereby deflecting the joint 222 a second distance 328 to the side of the sheath 308 greater than the first distance 322. This may be implemented with the elements of Examples 15 through 19 alternatively or in addition to one another.

All features and modifications of the described examples and dependent claims are usable in all aspects of the examples taught herein. Furthermore, the individual features of the dependent claims, as well as all features and modifications of the described examples are combinable and interchangeable with one another.

What is claimed is:

1. A medical device snare, comprising:
a first strip extending from a first proximal end to a first distal end and having a first interlock feature configured as a groove extending from proximate the first proximal end to the first distal end;
a second strip extending from a second proximal end to a second distal end and having an intermediate point disposed between the second proximal end and the second distal end along a second strip longitudinal length, the second strip having a strip portion extending from the second proximal end to the intermediate point and having a second interlock feature configured as a rail extending from the second proximal end and terminating at the intermediate point, the strip portion defining a strip portion longitudinal length, the second strip having a snare portion extending from the intermediate point to the second distal end, the snare portion defining a snare portion longitudinal length, the strip portion longitudinal length being at least ten times the snare portion longitudinal length, the first distal end and the second distal end being fastened together at a joint to prevent parallel movement of the first strip and the second strip at the joint; and,
wherein the first interlock feature configured as a groove and the second interlock feature configured as a rail are interlocked such that the first strip and the second strip are slidable parallel to one another along the strip portion, and the snare portion is not interlocked with the first strip so the snare portion forms a loop when at least one of the first strip and the second strip slides relatively parallel to the other.

2. The medical device snare of claim 1, wherein the first strip comprises a working channel extending from the first proximal end to the first distal end.

3. The medical device snare of claim 1, wherein the second strip comprises a working channel extending from the second proximal end to the second distal end.

4. The medical device snare of claim 1, comprising a sheath, the first strip and second strip being disposed within the sheath.

5. The medical device snare of claim 1, comprising a sheath, the sheath terminating proximate the joint, the sheath being retractable to expose at least a part of the snare portion.

6. The medical device snare of claim 1, wherein the first strip and the second strip are polymeric.

7. The medical device snare of claim 1, wherein the first strip and the second strip are polymeric and at least a portion is radiopaque.

8. The medical device snare of claim 1, wherein at least a portion of the first strip and second strip are echogenic.

9. The medical device snare of claim 1, comprising a handle fixed to one of the first strip and the second strip, and the other of the first strip and the second strip is fixed to an actuator slidably received within the handle.

10. A method for using a medical device snare:
inserting a medical device snare into a body passageway, the body passageway having an object, the medical device snare comprising:
a first strip extending from a first proximal end to a first distal end and having a first interlock feature configured as a groove extending from proximate the first proximal end to the first distal end;
a second strip extending from a second proximal end to a second distal end and having an intermediate point disposed between the second proximal end and the second distal end along a second strip longitudinal length, the second strip having a strip portion extending from the second proximal end to the intermediate point and having a second interlock feature configured as a rail extending from the second proximal end and terminating at the intermediate point, the strip portion defining a strip portion longitudinal length, the second strip having a snare portion extending from the intermediate point to the second distal end, the snare portion defining a snare portion longitudinal length, the strip portion longitudinal length being at least ten times the snare portion longitudinal length, the first distal end and the second distal end being fastened together at a joint to prevent parallel movement of the first strip and the second strip at the joint; and,
wherein the first interlock feature configured as a groove and the second interlock feature configured as a rail are interlocked such that the first strip and the second strip are slidable parallel to one another along the strip portion, and the snare portion is not interlocked with the first strip so the snare portion forms a loop when at least one of the first strip and the second strip slides relatively parallel to the other; and
a sheath extending from a proximal sheath end to a distal sheath end, the first strip with the snare portion being disposed within the sheath with the joint proximal the distal sheath end;
exposing part of the first strip and at least part of the snare portion and the joint outside of the sheath at the distal sheath end;
sliding at least one of the first strip and the second strip parallel relative to the other to form the loop at the distal sheath end, the loop defining a first span thereby deflecting the joint a first distance to a side of the sheath;
snaring the object; and,
sliding the at least one of the first strip and the second strip parallel relative to the other to contract the loop around the object.

11. The method of claim 10 comprising a handle fixed to one of the first strip and the second strip, and the other of one of the first strip and second strip is fixed to an actuator slidably received within the handle.

12. A method for using a medical device snare, comprising:

inserting a medical device snare into a body passageway, the body passageway having a side branch, the medical device snare comprising:
  a first strip extending from a first proximal end to a first distal end and having a first interlock feature configured as a groove extending from proximate the first proximal end to the first distal end;
  a second strip extending from a second proximal end to a second distal end and having an intermediate point disposed between the second proximal end and the second distal end along a second strip longitudinal length, the second strip having a strip portion extending from the second proximal end to the intermediate point and having a second interlock feature configured as a rail extending from the second proximal end and ending at the intermediate point, the strip portion defining a strip portion longitudinal length, the second strip having a snare portion extending from the intermediate point to the second distal end, the snare portion defining a snare portion longitudinal length, the strip portion longitudinal length being at least ten times the snare portion longitudinal length, the first distal end and the second distal end being fastened together at a joint to prevent parallel movement of the first strip and the second strip at the joint; and,
  wherein the first interlock feature configured as a groove and the second interlock feature configured as a rail are interlocked such that the first strip and the second strip are slidable parallel to one another along the strip portion, and the snare portion is not interlocked with the first strip so the snare portion forms a loop when at least one of the first strip and the second strip slides relatively parallel to the other; and
  a sheath extending from a proximal sheath end to a distal sheath end, the first strip and the snare portion being disposed within the sheath with the joint proximal the distal sheath end;
  exposing part of the first strip and at least part of the snare portion and the joint outside of the sheath at the distal sheath end;
  sliding at least one of the first strip and the second strip parallel relative to the other to form the loop at the distal sheath end, the loop defining a first span thereby deflecting the joint a first distance to a side of the sheath to direct the joint into the side branch.

13. The method of claim 12, comprising pushing the loop into the side branch.

14. The method of claim 12, comprising pushing the loop and the sheath into the side branch.

15. The method of claim 12, comprising twisting the medical device snare.

16. The method of claim 12, comprising a handle fixed to one of the first strip and the second strip, and the other one of the other first strip and the second strip is fixed to an actuator slidably received within the handle.

17. The method of claim 12, comprising:
  exposing a larger part of the first strip and a larger part of the snare portion outside of the sheath;
  sliding at least one of the first strip and the second strip parallel relative to the other to form the loop at the distal sheath end to define a second span greater than the first span, and thereby deflecting the joint a second distance to the side of the sheath greater than the first distance.

18. A medical device snare, comprising:
  a first strip comprising a first proximal end, a first distal end, and a first interlock feature configured as a groove extending from proximate the first proximal end to the first distal end;
  a second strip comprising a second proximal end, a second distal end, an intermediate point defined between the second proximal end and the second distal end, a proximal strip portion extending from the second proximal end to the intermediate point and having a second interlock feature configured as a rail, the second interlock feature extending from the second proximal end along a length of the second strip portion and terminating at the intermediate point, and a distal strip portion extending distally from the intermediate point to the second distal end, wherein the first strip and the second strip are joined at the respective first distal end and second distal end, wherein the first interlock feature and the second interlock feature are interlocked to prevent lateral separation between the first strip and the proximal strip portion of the second strip, and wherein the first strip and the distal strip portion of the second strip are laterally separable to form a snare portion; and
  a handle coupled to one of the first strip or the second strip, wherein the handle is configured to advance or retract one of the first strip or the second strip relative to the other of the first strip or the second strip.

19. The medical device snare of claim 18, further comprising a sheath encircling the first strip and the second strip, wherein the sheath is configured to prevent lateral separation between the first strip and the distal strip portion of the second strip when the sheath is advanced over a covered section of the snare portion.

20. The medical device snare of claim 19, wherein a proximal end of the sheath is coupled to the handle.

21. The medical device snare of claim 20, wherein the handle is configured to advance or retract the sheath relative to the first strip and the second strip.

22. The medical device of claim 19, wherein a position of the sheath over the snare portion determines a shape of the snare portion.

* * * * *